United States Patent [19]

Vettori de Almeida Rodrigues

[11] 4,351,615
[45] Sep. 28, 1982

[54] DIFFERENTIAL DILATOMETER

[76] Inventor: Carlos A. Vettori de Almeida Rodrigues, 30, rue Gassendi, 75014 Paris, France

[21] Appl. No.: 201,754

[22] Filed: Oct. 29, 1980

[30] Foreign Application Priority Data

Nov. 5, 1979 [FR] France ............................... 79 27215

[51] Int. Cl.³ .......................................... G01N 25/15
[52] U.S. Cl. ..................................................... 374/56
[58] Field of Search ............................................ 73/16

[56] References Cited

U.S. PATENT DOCUMENTS

| 2,559,789 | 7/1951 | Peckham | 73/16 |
| 3,474,658 | 10/1969 | Levy et al. | 73/16 |
| 3,583,208 | 6/1971 | Byrne, Jr. | 73/16 |
| 3,589,167 | 6/1971 | Hill | 73/16 |

FOREIGN PATENT DOCUMENTS 1134086 11/1968 United Kingdom ................... 73/16

OTHER PUBLICATIONS

Gurevich et al., "An Absolute Opticomechanical Low-Temp. Dilatometer Based on a Relative Dilatometer", in Inst. & Experimental Techniques, vol. 18, #2, 1975, pp. 622, 623.

Primary Examiner—Herbert Goldstein
Attorney, Agent, or Firm—Brisebois & Kruger

[57] ABSTRACT

A differential dilatometer for simultaneously measuring the relative expansion of two different solid test samples, one of which can be a reference sample. The test sample and the reference are mounted in a support tube and suspended from a head, and the variation in length of the samples is transferred by two push rods connected respectively to the coil and core of a differential transformer. The support tube is inside a cryostat to permit circulation of a cryogenic fluid, during measurements. An electric heating sleeve inside the cryostat provides for further temperature regulation. Both the push rods and the support tube are of vitreous silica. The heating sleeve is supported by the head via thermal insulation, and the head is supported by a vibration absorbing mount.

10 Claims, 5 Drawing Figures

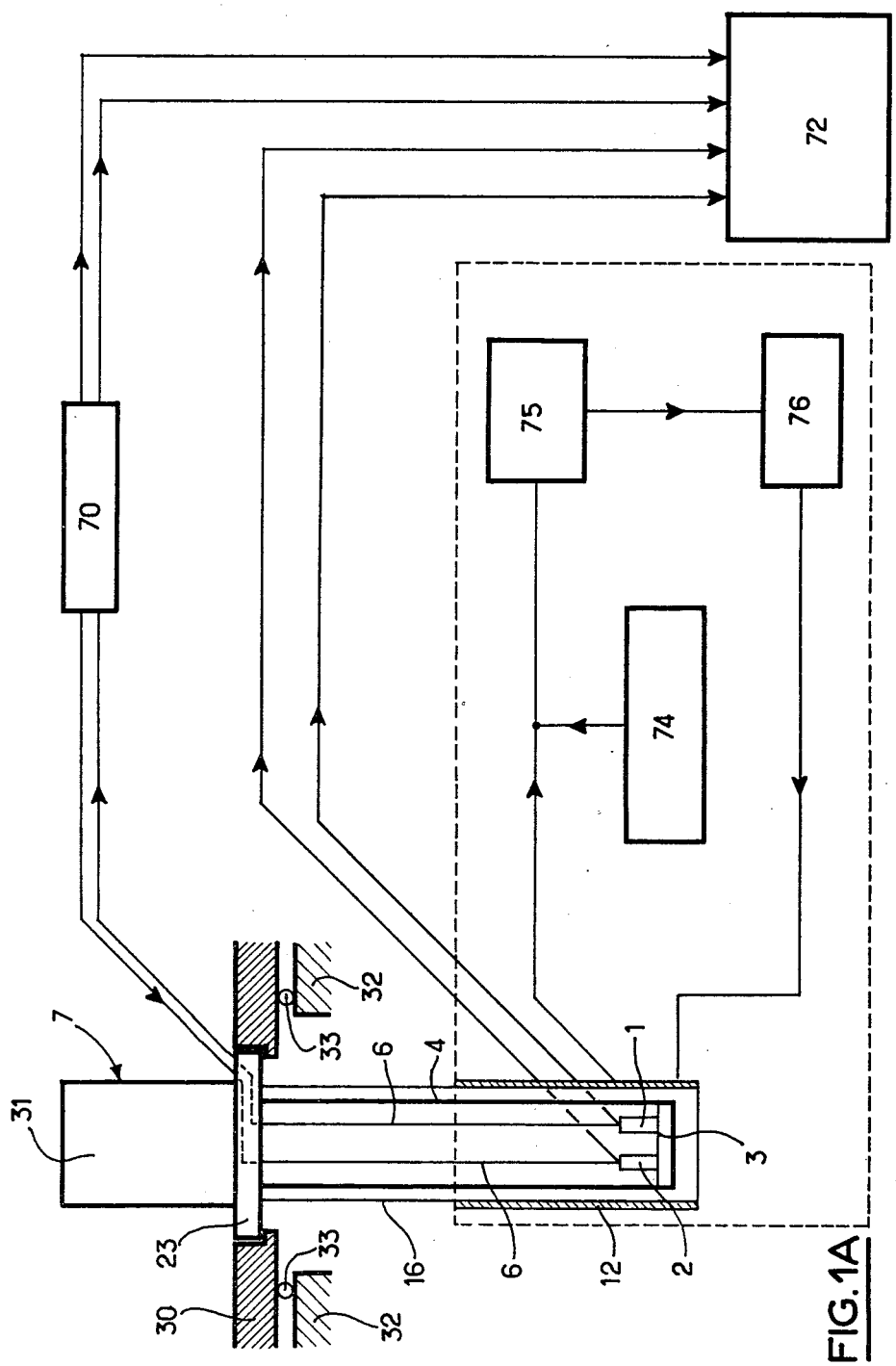

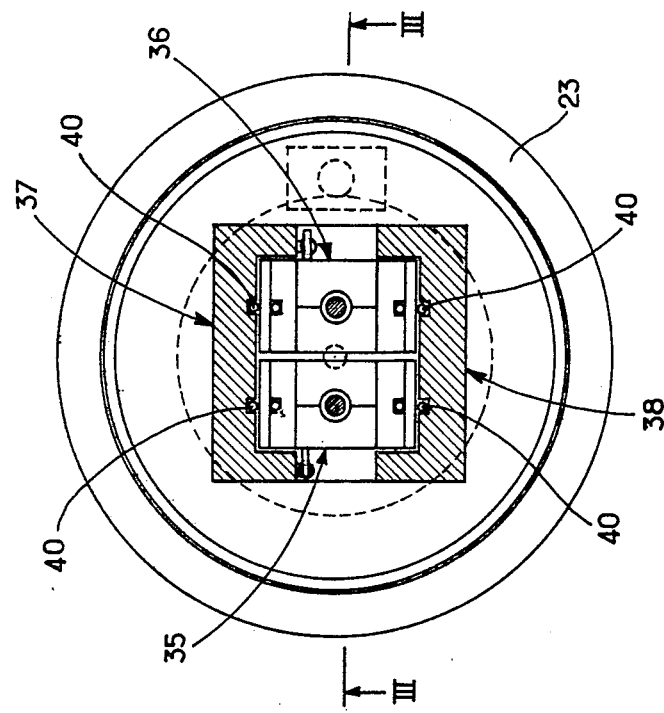
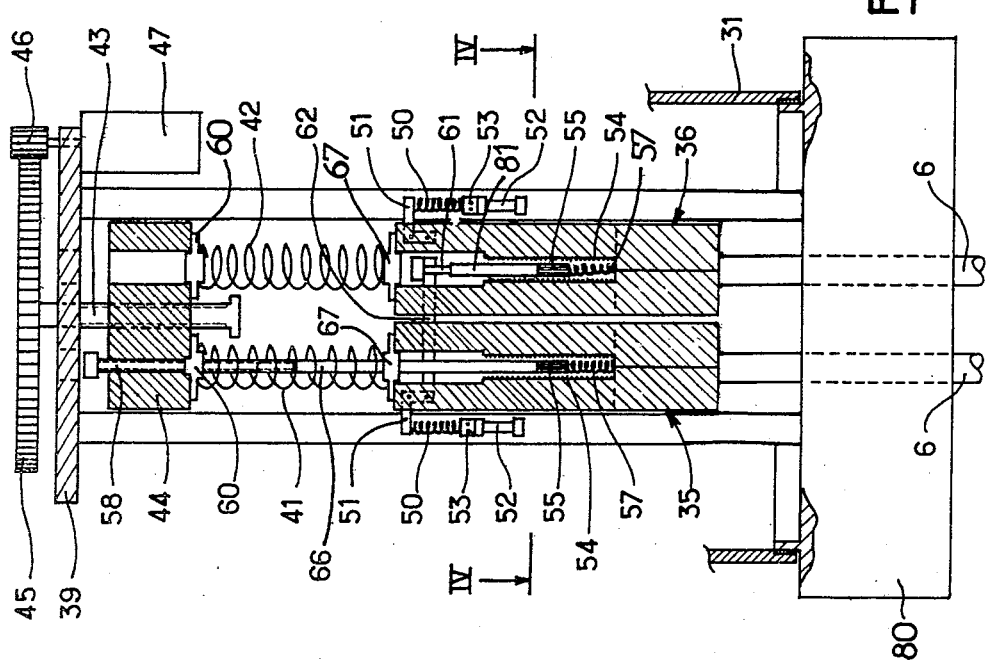

DIFFERENTIAL DILATOMETER

This invention relates to measuring instruments such as dilatometers and more particularly to differential dilatometers for simultaneously measuring dimensional changes of two different solid test samples, one of which may be a reference sample whose thermal expansion is accurately known. Some typical applications of dilatometers are: to measure the linear thermal expansion of solids; to detect phase transformations in a material; to measure changes in the crystallographic structure of a material; and to study the compatibility of materials under changing temperature variations.

In an ordinary differential dilatometer the thermal expansion of a solid test sample is measured relative to that of a reference material. The sample and the reference are mounted in a support tube and their dimensional changes are transmitted by two push rods to a displacement transducer which measures the differential expansion. In this respect it is possible to point out three types of transducers according to their operating principle: mechanical; optical; or electrical. The electric displacement transducer is particularly interesting because it allows notable amplification of the dimensional changes of samples, especially in the case where the latter have an extremely low coefficient of thermal expansion. The electric displacement transducer can be a linear variable differential transformer. The differential transformer changes the variation in length of the tested sample into an electrical signal and a demodulator conditions the resulting signal for suitable recorder display.

The present invention aims at describing a differential dilatometer, of the type having a linear variable differential transformer and push rod means, upon which the following improvements were brought about:

A vitreous silica support tube is mounted inside a cryostat allowing the circulation of a cryogenic fluid, such as liquid helium, around the test sample and the reference. Due to such a cryostat, the dilatometer comprising this invention is capable of operating at very low temperatures which can be as low as 4° K.

To assure the maintenance of a homogeneous temperature in the region where the test sample and the reference are mounted, a vertical disposition is adopted, the cryostat which encloses the support tube being placed below the measuring head, so that during the circulation of the cryogenic fluid, the place where the test sample and the reference are situated had the lowest temperature.

In order to study the dilatometric behavior as a function of the temperature of the test sample, for instance in the (4–500)°K. temperature range, an electric heating sleeve, which surrounds the region of the support tube where the test sample and the reference are mounted, was embodied inside the cryostat. The amount of heat supplied by the electric heating sleeve is controlled by a regulation loop in which the signal delivered by a temperature sensor placed on the electric heating sleeve is compared to a variable reference signal given by a programmable dc-voltage generator, the deviation signal between the temperature sensor and the generator is then sent after amplification to a power unit which feeds the electric heating sleeve. Hence, with a linearized temperature sensor, it is possible to attain linear cooling and heating of the sample and the reference in the temperature range of the apparatus.

The object of the present invention is not only to measure the relative expansion of two different solid test samples or their absolute expansion as a function of temperature and/or time, but also to measure the influence on the expansion of a solid test sample of an adjustable applied pressure on the test sample. To do so, each of the two push rods which transmit the expansion of the test sample and of the reference are associated, in the measuring head, to a slide in which an electric displacement transducer is mounted; each of the above mentioned slides is submitted to an adjustable applied force given by at least one spring, one of the two electric displacement transducers is used to measure the dimensional change of the spring and consequently to measure the applied force on the test sample, whereas the other electric displacement transducer is used to measure the differential expansion between the test sample and the reference. Thus, in the present invention a force, for example in the range of 0–1 N, can be applied to the test sample. Another feature of the present invention is that the above mentioned force can be modified even during an experiment by means of an electric driving motor.

Therefore, the object of the present invention is to provide an improved differential dilatometer for simultaneously measuring, particularly at low temperatures, the relative expansion of two different solid test samples, one of which may be a reference sample whose thermal expansion is accurately known or the absolute expansion of the above mentioned samples, the test sample and the reference being mounted in a support tube, the variation in length of the test sample and the reference being transferred by two push rods, which extend inside the above mentioned support tube, into the measuring head where one push rod supports the coil of a linear variable differential transformer and where the other push rod supports the core of the linear variable differential transformer, the output signal of said transformer being fed to an amplifier whose output is proportional to the differential expansion between the two test samples, characterized by the fact that the support tube and the two push rods are vertical, the support tube being situated below the measuring head; that the support tube is at least partially mounted inside a cryostat which allows the circulation of a cryogenic fluid, during measurements, around the test sample and the reference, the region of the support tube where the test sample and the reference are mounted being, furthermore, surrounded by an electric heating sleeve which is embodied inside the cryostat, the amount of heat supplied by the heating sleeve being controlled and regulated by means of a temperature regulation system, the said heating sleeve avoiding a direct contact between the cryogenic fluid and the test samples.

In one preferred embodiment of this invention, the dilatometer comprises temperature sensors whose purpose is to measure the temperature of one test sample and the temperature of the other test sample or the reference, the signal delivered by each of these temperature sensors as well as the output of the amplifier of the linear variable differential transformer which measures the relative variation in the length of the test sample in relation to the reference and the amplifier of the linear variable differential transformer which measures the force applied to the test sample being, for instance, the input of a multi-channel analog recorder and/or the input of an automatic data acquisition system interfaced or not with a micro/mini-computer and peripherals of the system; the apparatus may also include temperature sensors whose purpose is to measure an eventual temperature gradient on the test samples; the temperature regulation system consists of a regulation loop in which the output signal given by at least one linearized temperature sensor secured to the electric heating sleeve is compared to a reference signal that can be constant or vary as a function of time, for instance in a linear mode, which is given by a programmable dc-voltage generator, the deviation signal between the two above mentioned signals being fed to a power unit which in turn feeds the electric heating sleeve. It is understood that a linear temperature sensor is a sensor whose output is or is rendered linear as function of temperature.

It will be noted that in order to prevent the influence of a magnetic field on the test samples as well as on the temperature sensors, the winding of the electric heating sleeve is wound "two wires in hand" after bending the wire in a loop thus forming two coils which have inverse fields.

Conveniently, both push rods and the support tube are made of vitreous silica, whereas the electric heating sleeve is of a good heat conducting metal, such as copper, and is secured in its upper end to the base of a protection tube which is of a poor heat conducting material, such as stainless steel, which surrounds the support tube, the cryostat embodying the heating sleeve and the base of the protection tube. The cryostat, the protection tube and the electric heating sleeve are preferably suspended and removably secured, for example by screw means, to the lower part of a plate made of a poor heat conducting material, such as stainless steel, the dilatometer head being secured to and above the above-mentioned plate, the said plate being secured below a heavy platform which rests on a support frame and being supported by anti-vibration means, the support tube being supported by the dilatometer head. The protection tube and the electric heating sleeve delimit a chamber that connects with the region where the displacement transducer(s) is (are) situated, the said region being isolated from the exterior by a cover, in preference made of a poor heat conducting material, the said chamber having passageway means for eventually receiving a flow of gas, preferably a good heat conducting gas. Also, means are provided for maintaining a constant temperature in the region surrounded by the lid. Furthermore, it is possible, for instance, to realize a vacuum of $10^{-6}$ Torr, a static atmosphere or a dynamic atmosphere in the chamber.

An interesting feature of the present invention is that each of the two push rods is interdependent on a slide in its upper part, said slides being guided vertically by sliding guides with an axis parallel to that of the push rods, each slide bearing an applied force adjustable by spring means. The aforementioned springs can be adjustably compressed by the nut of a screw-nut system, said nut being guided in translation by the vertical sliding guides of the two slides, whereas the corresponding screw is stationary in relation to the aforementioned sliding guides and is interdependent on a cogwheel which engages with the pinion of an electric driving motor.

Both slides are preferably associated to an electric displacement transducer whose core can move in relation to the coil which is mounted in a slide; the slide of the push rod which bears on the test sample is responsive for the movement of the core of the electric displacement transducer mounted in the other slide, the position of the aforementioned core in relation to the coil being adjustable for zeroing purposes by means of an adjusting screw. The variation in length of the spring bearing on the test sample is transmitted to the core of the electric displacement transducer mounted in the slide of the push rod which is supported by the test sample, said transducer allowing to determine, after calibration, the intensity of the force applied by the spring on the test sample and to determine thereof that applied on the reference; straight above the slide of the push rod bearing on the test sample, the nut of the screw-nut system bears a screw which can move in relation to it, the aforementioned screw permitting the adjustment, by means of a rod which extends inside the related spring, of the position of the core in relation to the coil of the electric displacement transducer meant to determine the force applied on the test sample and the reference.

Another interesting feature of the present invention is that both push rod slides are supported by at least one weight compensating spring carried by their vertical sliding guides, the aforementioned spring allowing, through an adjusting screw, the adjustment of the position of each slide on its sliding guide and counterbalancing the weight of each sliding unit (slide+push rod).

The description of the invention that is given hereafter taken in conjunction with the accompanying drawings is an example intending only to illustrate and not to limit in any way the scope of the present invention.

In these drawings:

FIG. 1A is a schematic view of the differential dilatometer in an analog recording version comprising the invention;

FIG. 3 is a vertical schematic axial sectional elevational view of the dilatometer head taken along line III—III of FIg. 4; and FIG. 4 is a horizontal schematic sectional elevational view of the dilatometer head taken along the line IV—IV of FIG. 3.

Figure 1B:
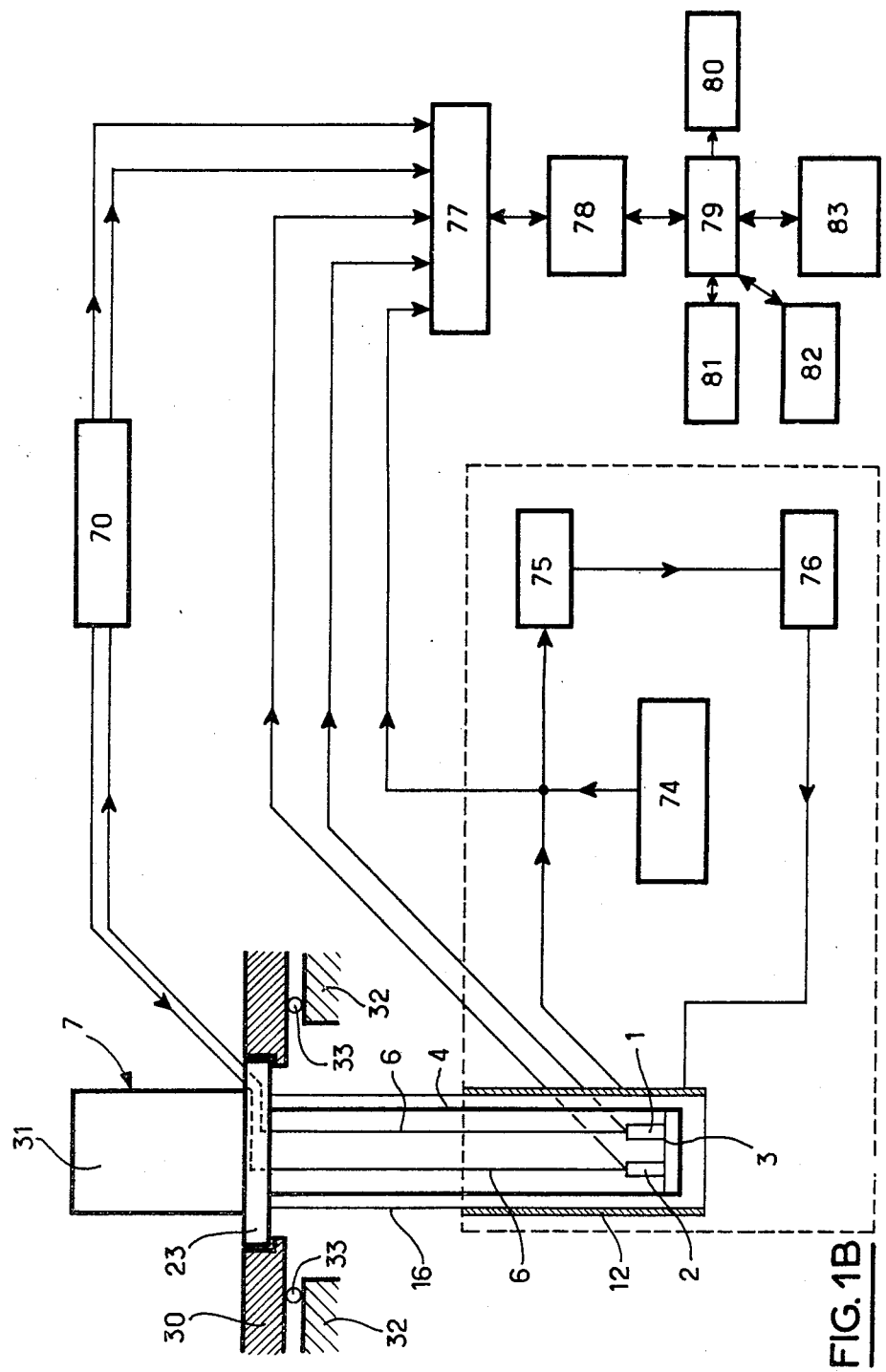
FIG. 1B is a schematic view of the differential dilatometer in a digital recording version comprising the invention.

Referring to the drawings, it will be seen that an instrument whose purpose is to simultaneously measure dimensional changes of two different solid test samples 1 and 2, one of which may be a reference sample whose thermal expansion is accurately known, has been represented (FIG. 2), the thermal expansion of the test sample being measured relative to that of the reference material. The test sample 1 and the reference 2 are mounted on a vitreous silica support platform 3 supported by a vitreous silica support tube 4. Two vitreous silica push rods 6 whose enlarged base sections are respectively supported by the reference 2 and the test sample 1 extend inside the support tube 4. As explained hereafter, the object of the two push rods is to transmit the variation in length of the reference 2 and the test sample 1 to two electric displacement transducers positioned inside the dilatometer head 7 (FIGS. 1A, B) above the support tube 4.

The dilatometer disclosed here as an example is intended more particularly to study dimensional changes of alloys (iron-nickel-carbon), in the 4° to 500° K. temperature range, in order to understand the austenite to martensite transformation of alloys which have a low Ms (below room temperature), as well as connected phenomena. The vitreous silica support tube 4 is therefore embodied inside a cryostat 8 allowing the circulation of cyrogenic fluid such as liquid nitrogen or liquid helium around the test sample 1 and the reference 2. The body of the cryostat 9 has the overall shape of a cylinder with an open top and a closed bottom. An added assembly bridle 10 is fixed to the open top of the body of the cryostat 9. An inlet 11 is connected at right angle to the body of the cryostat 9. Through the open end of the inlet 11 the transfer tube (not shown) is inserted for transferring the liquid nitrogen or liquid helium from a container in the body of the cryostat 9.

The test sample 1 and the reference 2 can also be heated by means of an electric heating sleeve 12 consisting of a unifilar heating element wound around a copper tube. The heating sleeve 12 is inserted within a closed cylindrical case 13a whose base 13b includes an adjutage 14 permitting the introduction of the cryogenic fluid. The heating sleeve 12 is positioned around the lower part of the support tube 4 where the test sample 1 and the reference 2 are mounted; its upper part is brazed 15 to a stainless steel protection tube 16.

The cryogenic fluid introduced through the open end of the inlet 11 travels through an internal tube connected to the adjutage 14, which is situated on the base 13b, by passageway means 17. The adjutage 14 is situated below the electric heating sleeve 12; the cryogenic fluid coming from the adjutage 14 goes through the perforated lower wall of a copper cover 18a interdependent on the case 13a an ascends within the body of the cryostat 9 to escape through outlet 18b positioned on the upper part of the cryostat, right beneath its assembly bridle 10. The circulation of cyrogenic fluid within the cryostat 8 can be improved by using a circulation pump connected to outlet 18b.

A thermocouplet 19 of the type (Au/Fe-Ni/Cr) is secured onto the electric heating sleeve 12 while two other thermocouples 21, 20 are respectively secured onto the reference 2 and the test sample 1. Thermocouples 20, 21 are brought out of the cryostat 8 through the open upper end of the cryostat 8 and through passageway means provided in the wall of disk 22. Thermocouple 19 is brought out of the cryostat 8 through the protection tube plate 26.

Figure 2:
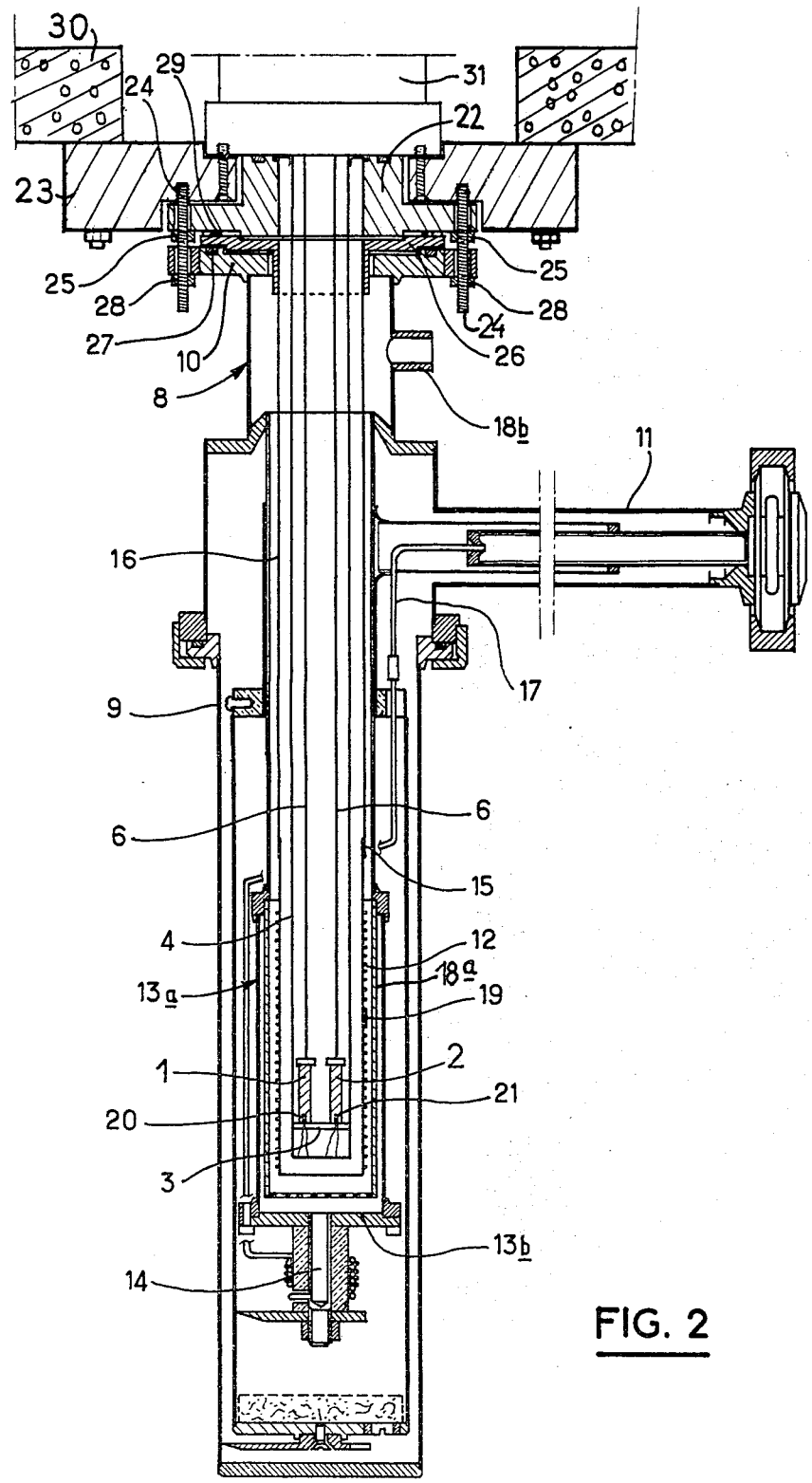
FIG. 2 is a vertical axial sectional elevation of the lower part of the dilatometer which includes the support tube and the cryostat.

The support tube 4, the protection tube 16 connected in its lower part to the heating sleeve 12, as well as the cryostat 8, are encased coaxially. The protection tube 16 and the heating sleeve 12 as well as the cryostat 8 are suspended and fixed to a plate 23; the disk 22 is mounted inside the cylindrical cavity of plate 23 and is fixed by means of threaded rods 24 and nuts 25; the protection tube plate 26 which is fixed to the upper end of the protection tube 16 rests on an O-ring 27 situated on the assembly bridle 10 of the cryostat 8. Circular holes in equal number to the threaded rods 24 are provided at the periphery of the assembly bridle 10. Once disk 22 has been secured to plate 23, by the tightening of bolts 25 on the threaded rods 24, the assembly bridle 10 on which the protection tube plate 26 rests, can be secured by inserting the threaded rods 24 inside the aforementioned circular holes of the assembly bridle 10 and by tightening the hole unit by means of nuts 28. As can be seen in FIG. 2, before assembling, an O-ring 29 is positioned between disk 22 and the protection tube plate 26.

The plate 23, above which the dilatometer head is screwed and under which the cryostat 8, the protection tube 16 and the heating sleeve 12 are suspended, is secured below a heavy support platform 30, which rests on a heavy support frame 32 by means of three pneumatic insulators 33 (FIGS. 1A, B) used to reduce the effect of external vibration on measurements. The instrument center of gravity is approximately situated within the plane defined by the three pneumatic insulators 33.

The two vitreous silica push rods 6 go through plate 23 and project inside a cylindrical cover 31 (FIGS. 1A, B and 3) which encloses the dilatometer head 7. The cover 31 is removable; it is screwed onto the base 80 of the dilatometer head 7. The zone enclosed by the cover 31 is thermally stabilized by means of a thermostatically controlled circulator (not shown). The upper end of the two push rods 6 jutting above plate 23 is interdependent on a slide 35, 36.

The two slides 35 and 36 are guided along the displacement axis of the push rods 6 by two vertical sliding guides 37, 38 connected to the base 80 and to a crosspiece 39 in their upper part. As can be seen in FIG. 4, the two sliding guides 37, 38 have a U-shaped section; their legs face each other and are coplanar; in the inside of the U-shaped sliding guides, two vertical grooves 40 receive a ball bearing unit. The object of the ball bearing unit is to reduce as much as possible the frictions of the slides 35, 36 on the sliding guides 37, 38.

The upper wall of the two slides 35, 36 co-operates with a spring 41, 42, allowing an adjustable force to be applied on the test sample 1 and the reference 2. The two calibrated springs 41, 42, can be compressed by means of a screw-nut system 43, 44. In this system, the rotation of the screw 43 drives the translation of the nut 44 guided by the two sliding guides 37, 38. The screw 43 can rotate inside the crosspiece 39; its upper end is interdependent on a cogwheel 45 which engages with the pinion 46 of an electric driving motor 47, also supported by the crosspiece 39. The electric driving motor 47 can run in either direction. Therefore, starting the motor 47 can either drive up or down the nut 44 of the screw-nut system bearing the two springs 41, 42. The measurement of the expansion or the contraction of the calibrated spring 41, by means of an electric displacement transducer described hereinafter, permits the determination, after calibration, of the intensity of the force applied on the test sample 1 and thereof the determination of the force applied on the reference 2.

Both slides 35 and 36 are provided with a system intended to compensate the weight of the slide and corresponding push rod 6 as well as the friction forces of the slide on the sliding guides 37, 38. Such a system consists of a spring 50 which has an effect on a bracket 51 secured to slide 35, 36. The supporting action of spring 50 can be adjusted by means of an adjusting screw 52 which can have a helicoidal movement in relation to an associated nut 53, fixed to the vertical sliding guide 37.

Both slides 35, 36 have the overall shape of a rectangular parallelepiped, with a well in their vertical axis of symmetry. The coil 54 of an electric displacement transducer is positioned within each of the aforementioned wells. A ferrite core 55 can be displaced in each transducer, as a function of the variation in length which is to be measured, in relation to the associated coil 54. The object of the electric displacement transducer associated to slide 36 is to determine the relative variation in length of the test sample 1 in relation to the reference 2, whereas the electric displacement transducer associated to slide 35 is used to measure the variation in length of spring 41, and subsequently the variation of the intensity of the force applied on the test sample 1 by this spring.

In the electric displacement transducer 35, the ferrite core 55 is fixed to the lower end of a vitreous silica rod 66. A spring 57 is inserted between the lower end of the ferrite core 55 and the bottom of the well. At its upper end, the vitreous silica rod 66 juts axially inside 35; it passes freely through a hollow plug 67, which rests on the opening of the well, against which spring 41 bears; the vitreous silica rod 66 extends inside spring 41; and adjusting screw 58 screwed to the tapped hole of nut 44 of the screw-nut system (43-44) bears on the upper end of the spring. A hollow plug 60 holding the upper end of spring 41 is also screwed to the lower outlet of the tapped hole. The adjusting screw 58 can pass freely through the hollow plug 60 and move with a helicoidal movement, when acted on its head, in relation to nut 44 of the screw-nut system (43-44). Thus, it can be understood that the adjusting screw 58 permits the movement, against the spring 57, of the ferrite core 55 in coil 54 of the electric displacement transducer.

The ferrite core 55 of the electric displacement transducer associated to slide 36 is interdependent, by means of a small vitreous silica rod 81, on an adjusting screw 61, supported by a coupling tab 62 secured on slide 35. The adjusting screw 61 can have a helicoidal movement in relation to the coupling tab 62, thus allowing to adjust the relative position of the ferrite core 55 in relation to the corresponding coil 54.

The variation in length of the test sample 1 transmitted by the corresponding push rod 6, produces an equal displacement of slide 35, and consequently of the associated coil 54, in relation to the ferrite core 55 which remains stationary. The aforementioned displacement of slide 35 produces the concomitant displacement, by means of the coupling tab 62, of the ferrite core 55 in relation to slide 36, and consequently in relation to the associated coil 54. Obviously, the variation in length of the reference 2, transmitted by its push rod 6, produces a corresponding movement of slide 36, and consequently of coil 54 which is supported by it, in relation to the ferrite core 55 which is interdependent in its movement on slide 35. Therefore, it can easily be seen that the relative displacement of the ferrite core 55 within the coil 54 of the electric displacement transducer associated to slide 36 allows the measurement of the relative variation in length of the test sample 1 in relation to the reference 2.

Before measuring the dilatometric behavior of the test sample 1, the adjustment of the force applied by the two push rods 6 on the reference 2 and the test sample 1 is made by starting the electric driving motor 47 which allows, by means of the nut 44 of the screw-nut system (43-44), to depress more or less the two springs 41, 42. After zeroing, the expansion or the contraction of the spring 41 induces a corresponding movement of the ferrite core 55 in relation to the coil 54 of the slide 35. Since the variation in length of spring 41 is proportional to the applied force, the output signal given by the displacement transducer associated to slide 35 is representative of the applied force on the test sample 1. The applied force on the reference 2 is also given by the above-mentioned output signal.

The output signals of the two aforementioned and described electric displacement transducers are conditioned in an amplifier 70 (FIGS. 1A, B) which in turn can supply two output signals, one representative of the applied force on the test sample 1 and the other representative of the relative variation in length of the test sample 1 in relation to the reference 2. Both outputs of amplifier 70 are measured and recorded by suitable recording equipment such as an ordinary multi-channel analog recorder 72 as shown in FIG. 1A and/or by an automatic data acquisition system consisting of a scanner 77 and an analog to digital converter (ADC) 78 interfaced or not with a micro/mini-computer 79 and peripherals of the system which consist of a printer 80, a tape recorder 81, a floppy disk 82 and an X-Y graphics plotter 83 as shown in FIG. 1B. The e.m.f. of thermocouples 19, 20, 21 are measured and recorded as described above. Presently, in a measurement cycle, the following read and store measurements are made: the time which can be given by the micro/mini-computer; the differential expansion ($\Delta l$); the force applied by the push rod 6 on the sample; the temperature of the test sample 1 (Ts), of the reference 2 (Tr), and of the heating sleeve 12 (Ths) as shown in FIG. 1B. The mini-computer which is the data acquisition controller, controls the scanner and the ADC, stores and processes the acquired data, and outputs the results to the external peripherals of the system (plotter, printer, taperecorder, and floppy disk unit). It is to be understood that the measuring and recording equipment shown in FIGS. 1A and 1B are not mutually exclusive.

The dilatometer described above as an illustration of the present invention is operated as follows: the test sample 1 and the reference 2 are positioned on the support platform 3 of the support tube 4 which is secured to the base 80 of the head 7; then the unit comprising the protection tube 16 and the heating sleeve 12 as well as the cryostat 8 is mounted around the support tube 4 and is screwed below plate 23. The two weight compensating devices are adjusted manually by acting on screw 52 so that the enlarged section base of the two vitreous silica push rods 6 bears against the test sample 1 and the reference 2; then the nut 44 of the screw-nut (43-44) is lowered until the two hollow plugs 60 bear against the upper end of the two springs 41, 42; then the "electrical zeroing" of the electric displacement transducer associated to slide 35 is obtained by acting on the adjusting screw 58. The springs 41, 42 can then be compressed by means of the electric driving motor 47, the intensity of the applied force being measured and stored by the analog recorder 72, and/or the automatic data acquisition system 77, 78, 79, 80, 81, 82, 83, provided that the associated displacement transducer as well as springs 41, 42, have been previously calibrated. Then a rough electric zeroing of the electric displacement transducer associated to slide 36 is obtained by acting on the adjusting screw 61; a precise zeroing is obtained by acting on a potentiometer of amplifier 70. The protection cover 31 which had been removed to allow these manual adjustments, is then put back in place and if need be, the applied force can be modified by the driving motor 47.

The protection tube 16 and the heating sleeve 12 delimit a chamber that connects with the region where the two electric displacement transducers are situated, said region being thermally isolated from the exterior by the cover 31; the object of this chamber is to receive a flow of gas, preferably, which is good heat conducting, such as helium gas for instance. Furthermore, the region enclosed by the cover 31 is advantageously kept at a constant temperature by circulating a temperature controlled fluid.

One of the main features of the present invention is to provide a dilatometer for the study of the dilatometric behavior of a solid test sample by submitting said sample to linear variations in temperature. To this end, a temperature regulation system which controls the amount of heat supplied by the heating sleeve 12 is provided: as shown in FIGS. 1A, B, the e.m.f. of thermocouple 19 (Au/Fe-Ni/Cr) secured to the heating sleeve 12 is compared to a reference signal given by a programmable dc-voltage generator 74 whose output voltage can be a linear function of time. The deviation signal between the thermocouple 19 and the generator 74 is sent to a temperature regulator PID 75 (with proportional, integral and derivative actions) which, in its turn, outputs an amplified command signal to an actuator 76, here a thyristor power generator which feeds the electric heating sleeve 12. This allows, more particularly, with a circulation of liquid helium in the cryostat 8, to attain during experiments, linear heating or cooling of the test sample 1 and the reference 2 within a temperature range of 4° to 500° K. approximately. The test sample 1 and the reference 2 can moreover be kept at any given constant temperature within the aforementioned range for an indefinite period of time.

It is to be understood that the embodiment disclosed heretofore is not limiting in any way and any changes and modifications may be made thereto without departing from the spirit of the present invention; in particular, in an alternative embodiment, the screw 61 may either be directly accessible from the outside of the apparatus or driven by a stepper motor or by any other appropriate remote control unit; the mini-computer may also fully control the temperature regulation system of the differential dilatometer.

What I claim as new and desire to secure by Letters Patent is:

1. A differential dilatometer for simultaneously measuring, particularly at low temperatures, the relative expansion of two different solid test samples, one of which may be a reference sample whose thermal expansion is accurately known or the absolute expansion of the samples, the test sample and the reference being mounted in a support tube, the variation in length of the test sample and the reference being transferred by two push rods which extend inside the support tube, into a measuring head where one push rod supports the coil of a linear variation differential transformer and where the other push rod supports the core of the linear variable differential transformer, the output signal of said transformer being fed to an amplifier whose output is proportional to the differential expansion between the two test samples, wherein the support tube (4) and the two push rods (6) are vertical, the support tube being situated below the measuring head (7); the support tube (4) is at least partially mounted inside a cryostat (8) which allows the circulation of a cryogenic fluid, during measurements, around the test sample (1) and the reference (2), the region of the support tube (4) where the test sample (1) and the reference (2) are mounted being, furthermore, surrounded by an electric heating sleeve (12) embodied inside the cryostat (8), the amount of heat supplied by the heating sleeve (12) being controlled and regulated by means of a temperature regulation system, said heating sleeve avoiding a direct contact between the cryogenic fluid and the test samples, the electric heating sleeve (12) being secured at its upper end to the base of a protection tube (16) which is of a poor heat conducting material and which surrounds the support tube (4), the cryostat embodying the base of the protection tube (16), wherein both push rods (6) and the support tube (4) are made of vitreous silica, the electric heating sleeve (12) is of a good heat conducting metal, the protection tube (16) is made of stainless steel and is secured to the upper end of the heating sleeve (12), the protection tube (16) and the electric heating sleeve (12) are suspended and removably secured to the lower part of a plate (23) made of a poor heat conducting material, the dilatometer head (7) being secured to and above the plate, said plate being secured below a heavy platform (30) which rests on a support frame (32) supported by anti-vibration means (33), and the support tube (4) being supported by the dilatometer head (7).

2. Differential dilatometer according to claim 1, wherein said dilatometer comprises temperature sensors (20, 21) whose purpose is to measure the temperature of the test sample (1) and the temperature of the reference (2).

3. Differential dilatometer according to claim 1, wherein said temperature regulation system comprises a regulation loop in which the output signal given by at least one linearized temperature sensor (19) secured to the electric heating sleeve (12) is compared to a reference signal that can be constant or vary as a function of time, for instance in a linear mode, which is given by a programmable dc-voltage generator (74), the deviation signal between the two above mentioned signals being fed to a power unit (76) which feeds the electric heating sleeve.

4. Differential dilatometer according to claim 1, wherein the protection tube (16) and the electric heating sleeve (12) delimit a chamber that connects with the region where a displacement transducer is situated, the said region being isolated from the exterior by a cover (31) made of a poor heat conducting material, the said chamber having passageway means for receiving a flow of a good heat conducting gas.

5. Differential dilatometer according to claim 1, characterized by the fact that inside the dilatometer head (7), each push rod (6) is interdependent on a slide (35, 36) in its upper end, said slides being guided vertically by sliding guides (37, 38) with an axis parallel to that of the push rods (6), each slide (35, 36) bearing an applied force adjustable by spring means (41, 42).

6. Differential dilatometer according to claim 5, characterized by the fact that both springs (41, 42) acting on slides (35, 36) of both push rods (6) can be adjustably compressed by the nut (44) of a screw-nut system (43, 44), the nut (44) being guided in translation by the vertical sliding guides (37, 38) of the two slides (35, 36), whereas the corresponding screw (43) is stationary in relation to the said guides (37, 38) and is interdependent on a cogwheel (45) which engages with the pinion (46) of an electric driving motor (47).

7. Differential dilatometer according to claim 6, characterized by the fact that the nut (44) of the screw-nut system (43, 44) bears a screw (58) which can move in relation to it, the aforementioned screw permitting the adjustment, by means of a rod which extends inside the related spring (41), of the position of the core (55) in relation to the coil (54) of the electric displacement transducer meant to determine the force applied on the test sample (1).

8. Differential dilatometer in accordance with claim 5, characterized by the fact that both slides (35, 36) are each associated to an electric displacement transducer whose core (55) can move in relation to the coil (54) which is mounted in a slide.

9. Differential dilatometer according to claim 5, characterized by the fact that slide (35) of the push rod (6) which bears on the test sample (1) is responsive for the movement of the core (55) of the electric displacement transducer mounted in the other slide (36), the position of the aforementioned core (55) in relation to the coil (54) being adjustable by means of an adjusting screw (61).

10. Differential dilatometer according to claim 5 characterized by the fact that the variation in length of spring (41) bearing on the test sample (1) is transmitted to the core (54) of the electric displacement transducer associated to slide (35), said transducer allowing to determine, after calibration, the intensity of the force applied by the spring (41) on the test sample (1) and to determine that applied on the reference (2).

* * * * *